United States Patent [19]

Vegvari et al.

[11] 4,220,042
[45] Sep. 2, 1980

[54] MEASUREMENT OF CARBON BLACK DISPERSION

[75] Inventors: Paul C. Vegvari, Burlington; William M. Hess, Trenton; Vincent E. Chirico, Hamilton Sq., all of N.J.

[73] Assignee: Columbian Chemicals Company, Tulsa, Okla.

[21] Appl. No.: 23,577

[22] Filed: Mar. 26, 1979

[51] Int. Cl.$^2$ .................... G01N 19/08; G01N 33/34
[52] U.S. Cl. ................................................. 73/150 R
[58] Field of Search ......................... 73/159, 150, 105

[56] References Cited

U.S. PATENT DOCUMENTS

| | | | |
|---|---|---|---|
| 2,373,104 | 4/1945 | Dieffenbach | 73/150 |
| 2,688,532 | 9/1954 | Till et al. | 73/150 |
| 3,329,011 | 7/1967 | Dereng | 73/105 |
| 4,103,542 | 8/1978 | Wheeler | 73/105 |

*Primary Examiner*—S. Clement Swisher
*Attorney, Agent, or Firm*—Donald L. Traut

[57] ABSTRACT

A method is disclosed for determining the dispersion of carbon black in elastomeric slabs by cutting a slab to form a planar surface and moving a height measuring transducer stylus over the planar surface. The transducer stylus provides an output current at a voltage which varies in correspondence to the relative height of roughness peaks on the planar surface. Accordingly, the size of the peaks determines the size of carbon black agglomerates and the frequency of peaks for a predetermined range of height is determinative of percent dispersion of the carbon black.

4 Claims, 7 Drawing Figures

MEASUREMENT OF CARBON BLACK DISPERSION

BACKGROUND OF THE INVENTION

1. Field of the Invention

The invention pertains generally to a method of measuring and is particularly directed to determination of the degree of dispersion of fillers in polymeric substances. More particularly, it is directed toward determining dispersion ratings of carbon black in rubber.

2. Prior Art

It is well known to add carbon black as a reinforcing agent to rubber and other polymeric substances. To control the physical characteristics and quality of the mixture, it is necessary and desirable to determine the degree of dispersion of the carbon black in such polymeric substances.

Known prior dispersion measuring methods have included visual examination of freshly cut or torn surfaces of the carbon black stock thereby providing a rapid means of estimating the relative degree of dispersion. A well-dispersed stock shows a jet black, glossy surface and a stock having poor carbon black dispersion appears dull and graying. Unfortunately, this provides little quantitative data with which to distinguish two similarly dispersed stocks from one another.

Other prior known methods for determining dispersion which produce quantitative results include Tidmus and Parkinson, and Leigh-Dugmore. Tidmus and Parkinson, *Trans. Inst. Rubber Ind.* 13, 152 (1937), disclose a procedure in which a carbon black loaded rubber vulcanizate is frozen, cut into sections having a thickness of two microns and examined at a 100× magnification. Leigh-Dugmore, *Rubber Chem. Technol.* 29, 1303 (1956), disclosed an improvement wherein a calibrated grid divided into 10,000 squares is superimposed over the rubber section and the carbon black aggregates filling more than half of a square are visually counted. This value is divided by the total concentration of black in the stock, thereby giving a percent dispersion of carbon black in the rubber sample.

The time required to freeze the stock slab, to cut it into a thin section and to manually count the aggregates is a disadvantage. In addition, the counting of aggregates is left to the skill and eyesight of the operator and lack of consistency is a problem.

Also, since the slabs are cut manually, the thickness varies with each slab, and the count of agglomerates varies with the thickness.

SUMMARY OF THE INVENTION

It is therefore an object of this invention to provide quantitative data which relates to the percent dispersion of carbon black in polymeric substances. Another object of this invention is to provide percent dispersion results from masterbatch rubber and rubber incorporated with carbon black at low dispersion levels. A still further object of this invention is to provide data using a test which does not use a manual counter and which is automatic and reproducible.

In accordance with the present invention, a method for determining the degree of dispersion of carbon black in a rubber sample comprising contacting a surface of the rubber sample with a height measuring transducer means which supplies a current output at a voltage which varies in correspondence to the height of peaks on said sample surface, moving the contacted height measuring means over said sample surface, and recording the voltage output of the transducer as the transducer means moves up and down the surface peaks.

In addition, the present invention includes an apparatus for determining the degree of carbon black dispersion in elastomeric compounds which comprises:

a. a height measuring transducer which supplies electric current at a voltage which varies in correspondence to variations in height of peaks on a surface of a sample, the transducer having a surface contacting stylus thereon which contacts the surface being measured; and a thrust arm which is slidable back and forth;

b. a sample holder having a first sample-contacting face which opposes a second sample contacting face between which contacting faces the sample is held;

c. a driving means for tracing the transducer stylus at a controlled rate across the sample surface;

d. a force exerting means for pressuring the transducer stylus; and e. a means for determining the voltage of the electrical current supplied by the transducer during movement across the sample surface.

DETAILED DESCRIPTION OF THE DRAWINGS AND OF THE PREFERRED EMBODIMENT

Figure 1:
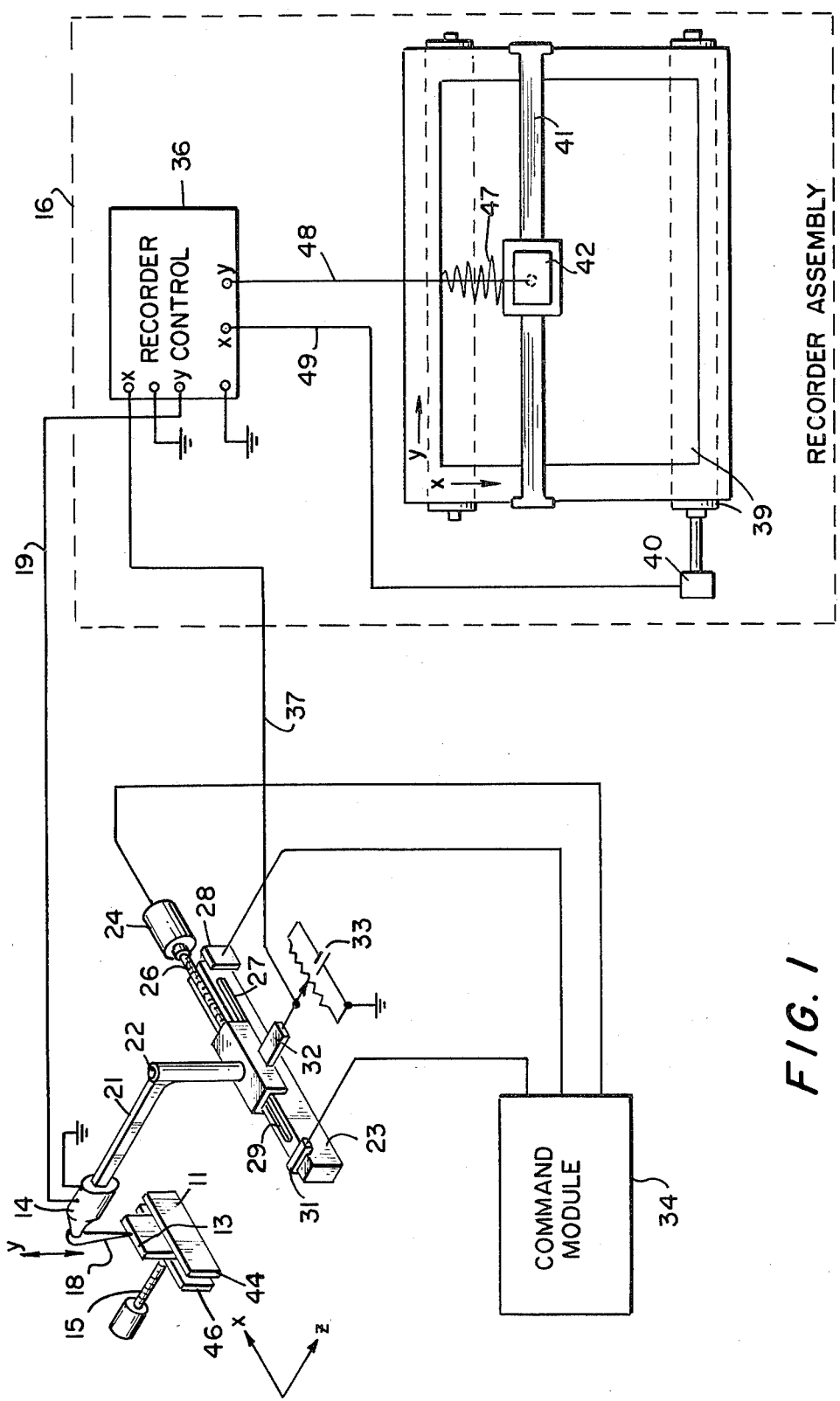
FIG. 1 is a schematic view of a dispersion analyzer apparatus constructed in accordance with the present invention.

Referring in detail to FIG. 1, the dispersion measuring device includes a holder 11 within which a stock rubber sample 12 having a planar surface 13 is mounted for scanning, a height measuring transducer 14 for scanning the planar surface and a recording assembly generally indicated by 16 for visually recording the scanning signal produced by the transducer 14.

The holder 11 consists of a first sample contacting face 44 which opposes a second sample contacting face 46 between which contact faces the sample 12 is held. The faces 44 and 46 are moved together by threaded means 15.

Figure 2:
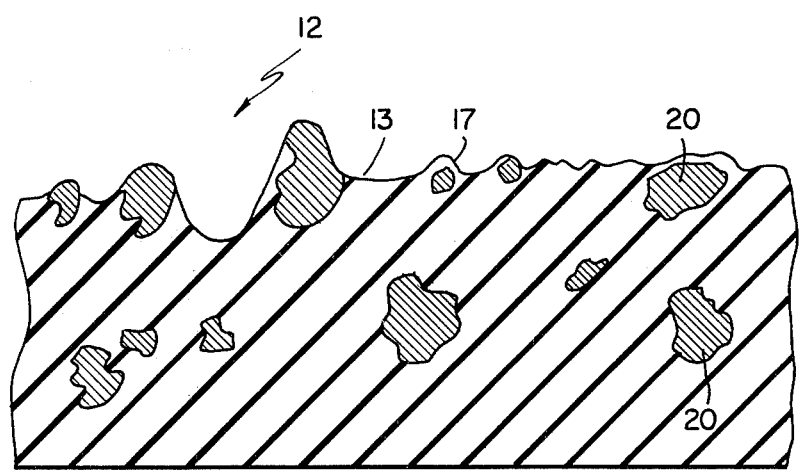
FIG. 2 is a section of rubber sample showing carbon black dispersions.

Referring in detail to FIG. 2, the planar surface 13 of the stock sample 12, although generally flat, contains irregular contour areas 17, generally hills and valleys, the hills being made up of carbon black agglomerations 20 dispersed in the stock rubber sample 12.

Movable to follow the contours of the planar surface 13, a stylus 18 is attached to a transducer 14. The transducer, sensitive to the y-axis movement of the stylus, converts the movement into a continuous electrical signal which is transmitted to the recorder assembly 16 via line 19. The signal is indicative of positive or negative y-axis excursions of the stylus away from the planar surface of the sample which is used as a reference.

The y-axis movement of the stylus is accomplished by mounting the stylus cantilevered from an arm 21 connected to a vertically reciprocal post 22. The post 22 is movable in the x-axis direction along a guideway 23 by action of a motor 24 and a threaded shaft 26. The movement of post 22 is limited by a first actuator finger 27 and a first switch 28, mounted at one extreme and a second actuator finger 29 and a second switch 31 mounted at the other extreme. The position of stylus 18 in the x-axis is determined by a potentiometer wiper 32 which moves along a potentiometer 33 coincidently with the stylus assembly movement along the guideway 23. The electrical signal so generated by the potentiometer is transmitted to the recorder assembly 16 by line 37.

A command module 34 receives position information from the limit switches 28 and 31 and directs scanning motor 24 as to the speed of the scan. The planar surface is generally scanned only in one direction for example, the negative x-direction and repositioned manually to the starting position.

The recording assembly 16 includes a recorder control 26, a movable recorder tape 39, a recorder tape control 40, and a mounting bar 41.

Additionally located on the mounting bar 41 is a pen station 42 movable along the y-axis of the recording tape 39. The recorder control 26 receives x-axis and y-axis signals via lines 19 and 37, respectively.

The y-axis signal is transmitted via line 48 from the recorder control to the pen station 42 moves the pen station along the y-axis. The x-axis signal is transmitted via line 49 from the recorder control to the recorder tape control 40 to advance the tape in the x-axis direction of the tape. These two signals provide a visual two axes (x-y) trace representation 47 of the surface of the stock sample 12.

From the trace representations, the average peak height, h, is determined by summing the height in microns of all roughness peaks greater than 0.5 micron and dividing by the number of peaks greater than 0.5 microns. Also from the trace representation, the number of peaks measuring greater than 0.5 micron, is divided by the length of the stylus trace in centimeters. The average peak height, h, and the frequency, f, are used in the following formula for calculation of Dispersion Index:

$$D.I. = 100 - f^2 h k_1 k_2$$

where $k_1$ is a proportionality constant based upon ASTM D-2663 light type microscope dispersion method and $k_2$ is a proportionality constant based upon operational parameters such as stylus force. For example, $k_1$ is 0.001 for a particular polymer, black loading and extender oil and loading, and $k_2$ is 1 for this system when the stylus force is 200 mg. The Dispersion Index number, although an absolute number, is useful primarily only when compared to a D.I. number obtained from a sample of a reasonably similar rubber, carbon black and carbon black loading.

The method of mechanically determining the degree of dispersion of carbon black in a rubber sample will now be more fully described.

A suitable cutting element is used to cut the stock sample to form a planar surface 13. The sample 12 is then secured within the holder 11 in such a manner that the planar surface 13 is in the x-z plane.

The stylus 18 is moved downward to contact the sample plane 13 and motor 24 is actuated to move the scan along the center line of the z-axis in the negative x-direction. The electrical signal generated by the transducer 14 is communicated to the recorder assembly where along with the position information from the potentiometer 33, the recorder pen provides a two-axis record of the planar surface contours.

Preferably, the uncured samples are pressed or sheeted out on a mill to a thickness of about 2 to 4 mm to remove the air holes prior to being inserted into the vise. The sides of the sheet should be parallel to avoid contortion in the surface structure.

More preferably, the uncured rubber is sheeted out to thickness (z-axis) of 2 or 3 mm.

The cutting of the sample plane 13 is to be performed at ambient temperatures, preferably between 20° C. and 30° C. The cutting instrument may be a commercial razor blade, the sharpness of which is not entirely critical. However, it is preferred that the the blade be replaced after about 25 cuts through well dispersed vulcanized compounds, about 10 cuts through uncured or low dispersion level compounds and about 2 cuts through compounds containing large particle size fillers and inorganic fillers such as clay, silica, calcium, carbonate, and iron oxide.

As an aid to the cutting step, the cutting instrument may be lubricated, to facilitate the cutting action. The use of a dissimilar oil with a particular rubber is preferred so as to prevent sample swelling. Silicone oil lubricants are preferred for hydrocarbon rubbers and hydrocarbon oil lubricants are preferred for silicone rubbers. The lubrication step tends to limit the degree of compression that would otherwise cause distortion of the sample and smearing of the agglomeration on or in the surface.

Normal surface roughness due to dull blades, imperfections in the cutting instruments or lack of lubrication is not critical to the readings obtained by the transducer stylus.

The cutting instrument should be positioned to give an angle between the cut planar surface and the side of the sample of 90° which will minimize the area of the planar surface and thereby limit the amount of cutting required.

The degree of compression of the sample by the holder faces 44 and 46 is not critical if the sample extension above the clamp is reasonable. A reasonable extension beyond the faces allows the sample to normalize between the clamped portion and the planar surface thereby providing a true reading of the concentration of the carbon black agglomerates at the surface. Preferably, this extension above the clamp ranges from 2 mm to 4 mm.

An angle A formed between and the planar surface the stylus along the z-axis should be between about 85° and 95°. Below 85° and over 95°, the stylus has a tendency to skip or jump over the surface causing irregular measurements. Preferably, the angle A is 90°. Measurements using angles other than 90° require a correlation of the height measurement with the new angle to determine the true height of the agglomerates as would have been measured with an angle A of 90°. Also resolution deteriorates since the stylus contacts a greater surface.

Angle B formed between the stylus and the planar surface along the x-axis should be between about 85° and 95°. Below 90°, the stylus would have a tendency to snag or hang up on the sample surface and above 95°, the stylus has a tendency to skip or jump over the surface causing measurement irregularities and would lose resolution. Preferably, the angle B is 90°. Measurements using angles other than 90° require a correlation of the height measurement with the new angle to determine true height of the agglomerates as would have been measured with an angle B of 90°.

The stylus tracking speed preferably ranges from about 0.025 mm/sec to about 2.5 mm/sec. More preferably, the speed is about 0.25 mm/sec.

The stylus tracking force ranges between about 50 mg and 800 mg. Preferably, the tracking force ranges from about 200 mg to about 800 mg. More preferably for cross-linked compounds, the tracking force is 200 mg.

Preferably, the height measuring transducer permits different measuring sensitivity levels so that the levels can be varied for a given compound type or dispersion level without significantly affecting the Dispersion Index accuracy.

A magnification factor which provides a full vertical scale on the recording tape of 20 microns is preferred for most carbon black dispersion levels. In compounds containing large amounts of inorganic fillers such as clay, calcium and iron oxide, a magnification factor providing 50 microns for the full scale is preferred. Since different magnification factors are specifically useful for production of tapes, that can be easily read, use of a computer and its memory reduces the need for such magnification factor changes.

The test method is conducted at ambient temperatures and pressures. Ideally, the samples should be maintained during the test procedure at a temperature between 20° C. and 30° C.

Although the recording assembly described hereinabove is a preferred form for the generation of signals for recording on the recorder assembly, it is understood that other devices could be used to accomplish the same task. For example, a computerized optical scan of the tape could be substituted for the mechanical scan illustrated in the above system. Furthermore, the recorder assembly could be replaced with a computer memory and computer analysis of the results.

Various types of transducers, transmitters, volt meter, power supplies, etc., can be used in the practice of the present invention. One advantageous combination of components is listed below:
Transducer-Gould Surfanalyzer 150
Recorder-Gould Surfanalyzer System 2000
Stylus Gould 21-3110-01 800 mg
Gould 21-3100-01 200 mg

EXAMPLE 1

70 pounds of a commercial N-339 carbon black having the following properties:
DBP Absorption, cc/100 g—120
Tint Strength—110
Surface Area, $N_2$, $m^2/g$—96 was blended with 100 pounds of SBR/BR rubber in accordance with conventional methods. Stock sample 1 was obtained by applying a mixing energy of 400 $MJ/m^3$. Samples 2, 3, 4 and 5 were obtained by applying mixing energies of 1150, 1565, 2000 and 2500 $MJ/m^3$, respectively.

Figure 3:
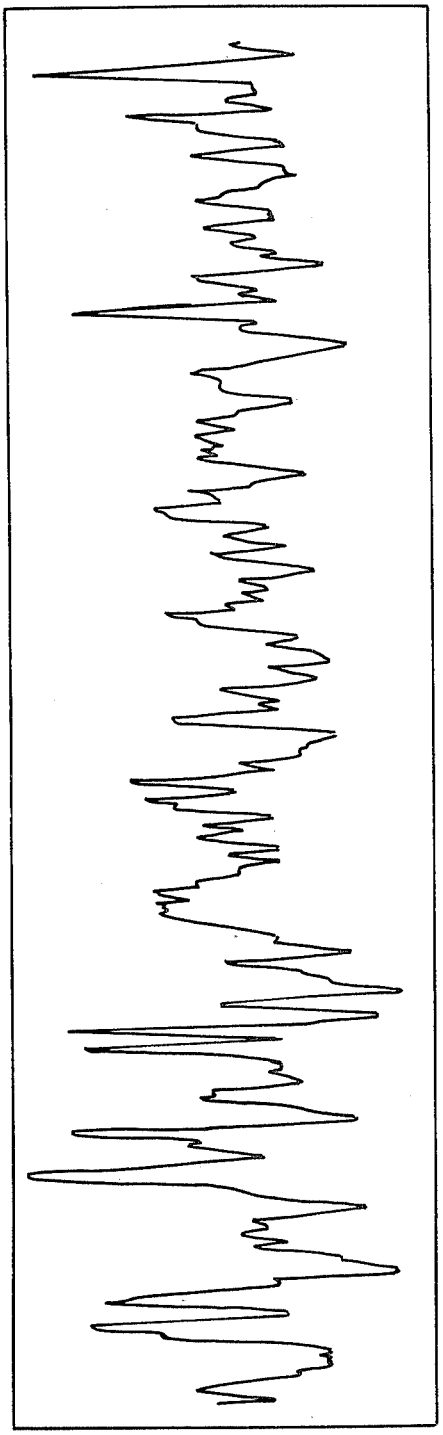
FIG. 3 is a representation of the results of a trace by the apparatus of FIG. 1 over an SBR/BR stock containing 31.7 wt % carbon black and showing 0% dispersion.
Figure 4:
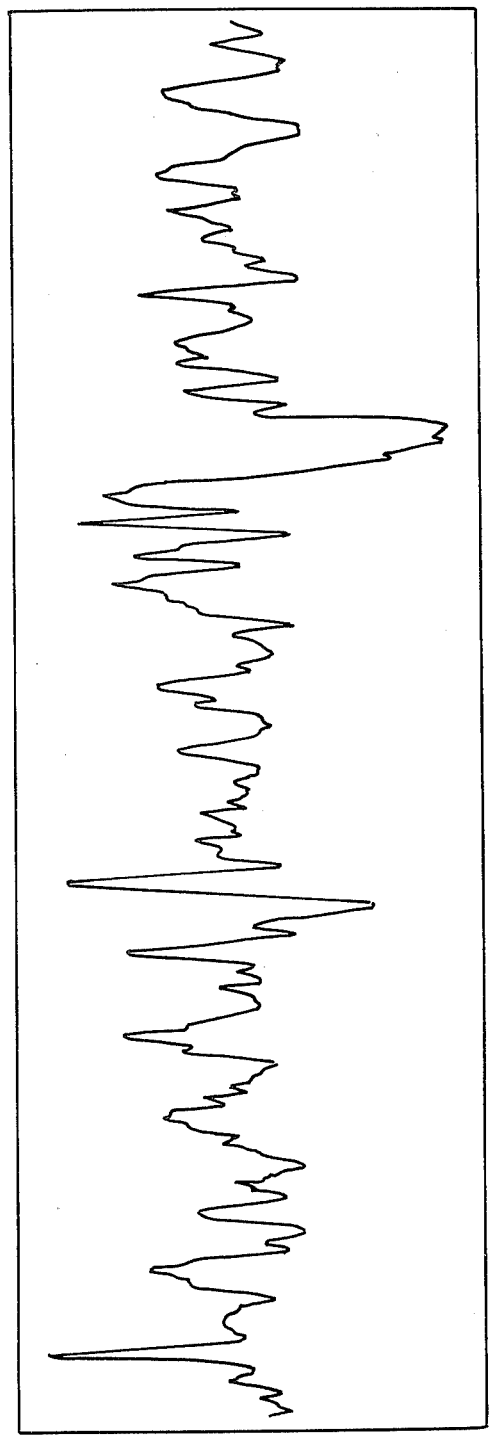
FIG. 4 is a representation of the results of a trace by the apparatus of FIG. 1 over an SBR/BR stock containing 31.7 wt % carbon black and showing 46.3% dispersion.
Figure 5:
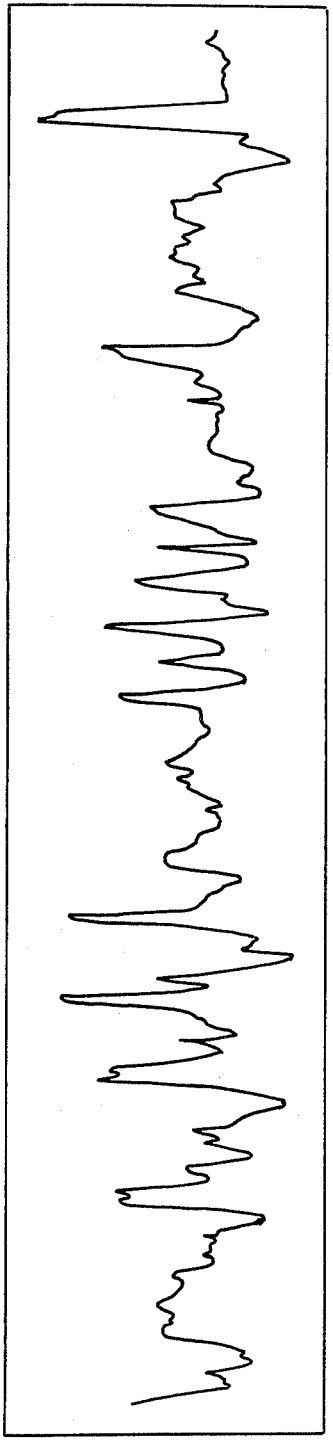
FIG. 5 is a representation of the results of a trace by the apparatus of FIG. 1 over an SBR/BR stock containing 31.7% carbon black and showing 61.0% dispersion.
Figure 6:
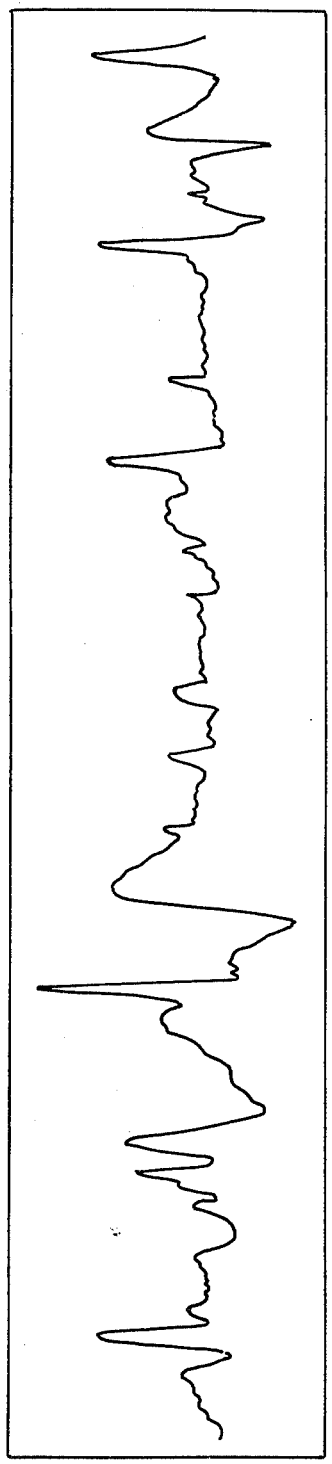
FIG. 6 is a representation of the results of a trace by the apparatus of FIG. 1 over an SBR/BR stock containing 31.7% carbon black and showing 87.3% dispersion.
Figure 7:
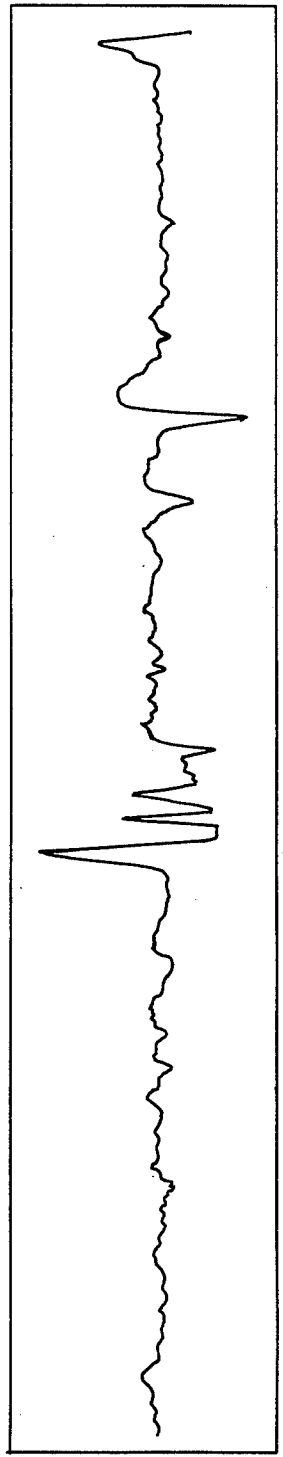
FIG. 7 is a representation of the results of a trace by the apparatus of FIG. 1 over an SBR/BR stock containing 31.7% carbon black and showing 95.6% dispersion.

The samples were sheeted to a thickness of about 2 mm using an 8"×18" 2-roll mill. Standard stress-stain slates (approximately 150×15×2 mm) were cured in a mold for 60 minutes at 145° C. and 7.8 MPa. A 10 mm by 30 mm section was then cut from each stock. A cutting element, described, above, was used to cut across the width and depth of the five sections thereby to providing a planar surface on each sample. One sample at a time was placed in the holder and secured so that the planar surface was situated in the horizontal x-z axes plane. The stylus was lowered into contact with the planar surface near the center of the z axis of the sample and the control motor was activated. The stylus was moved in an x-axis direction across the surface, generating electrical signals which were recorded with the position information from the potentiometer on the recording tape. Results from the scan of Sample 1 appear in FIG. 3. Sample 1 had an agglomerate frequency of 136.1/cm and an average height of 6.37 microns. This frequency and average height of Sample 1 produces an $f^2h$ of 117,993.

Samples 2, 3, 4 and 5 were scanned in sequence with the results of each scan appearing in FIGS. 4, 5, 6 and 7 respectively. The agglomerate frequency and average height for each sample appear in Table 1.

The length of time required for completion of the invention's method of dispersion determination ranged from 5 to 15 minutes per sample. Computer analysis of the transducer voltage outputs reduces the time of completion to 2 to 4 minutes per sample.

Separately, 5 sections were cut from stock samples 1, 2, 3, 4 and 5. The carbon dispersion levels of these five samples were measured in accordance with ASTM test procedure D-2663, the results of which appear in Table 1. The length of time required for completion of ASTM procedure D-2663 ranged from 10 to 40 minutes for each sample.

TABLE 1

|  | $f^2h$ | D.I. | D-2663 dispersion |
| --- | --- | --- | --- |
| Sample 1 | 117,993 | 0 | 0 |
| Sample 2 | 53,696 | 46.3 | 52.7 |
| Sample 3 | 38,998 | 61.0 | 65.9 |
| Sample 4 | 12,692 | 87.3 | 85.3 |
| Sample 5 | 4,430 | 95.6 | 95.1 |

While the invention has been described with reference to specific apparatus, components, combinations thereof, circuitry, sequences of operation, and the like, it will nonetheless be understood that other accordant embodiments will become apparent which are within the spirit and scope of the invention defined in the following claims.

What is claimed is:

1. A method for determining the degree of dispersion of carbon black in a rubber sample, comprising cutting said sample with a cutting element, thereby obtaining a sample surface, contacting (a) said surface of said rubber sample with a height measuring transducer, which supplies a current output at a voltage which varies in correspondence to the height of peaks on said sample surface, moving the contacted height measuring means across said sample surface, and recording the voltage output of said transducer as the transducer means moves up and down the surface peaks.

2. The method of claim 1 comprises positioning said sample surface so as to have a 90° angle between the transducer means and said sample surface.

3. The method of claim 2 comprises applying a tracking force of between about 100 and about 200 mg. to said height measuring transducer means.

4. The method of claim 3 comprises moving said height measuring transducer means moves across said sample surface at a rate of between about 0.1 mm/sec. and about 1 mm/sec.

* * * * *